(12) United States Patent
Parker

(10) Patent No.: US 9,981,081 B2
(45) Date of Patent: May 29, 2018

(54) TISSUE RETRACTOR

(71) Applicant: John Richard Parker, West Chester, PA (US)

(72) Inventor: John Richard Parker, West Chester, PA (US)

( * ) Notice: Subject to any disclaimer, the term of this patent is extended or adjusted under 35 U.S.C. 154(b) by 0 days. days.

(21) Appl. No.: 15/186,064

(22) Filed: Jun. 17, 2016

(65) Prior Publication Data

US 2017/0361012 A1     Dec. 21, 2017

(51) Int. Cl.
| | |
|---|---|
| *A61M 3/02* | (2006.01) |
| *A61M 1/00* | (2006.01) |
| *A61B 17/50* | (2006.01) |

(52) U.S. Cl.
CPC .......... *A61M 3/0237* (2013.01); *A61B 17/50* (2013.01); *A61M 1/007* (2014.02); *A61M 1/0064* (2013.01); *A61M 3/0262* (2013.01); *A61B 2017/505* (2013.01); *A61M 2202/20* (2013.01)

(58) Field of Classification Search
CPC .............. A61M 3/0237; A61M 3/0262; A61M 2202/20; A61B 17/50; A61B 2017/505
USPC ............................ 606/131; 604/294, 300, 68
See application file for complete search history.

(56) References Cited

U.S. PATENT DOCUMENTS

| | | | | |
|---|---|---|---|---|
| 3,507,274 A | * | 4/1970 | Soichet ................... | A61F 6/144 128/840 |
| 4,085,750 A | * | 4/1978 | Bosshold .............. | A61F 9/0026 604/302 |
| 4,767,416 A | * | 8/1988 | Wolf ................... | A61M 35/003 128/200.14 |
| 9,474,849 B2 | * | 10/2016 | Parker ................. | A61M 3/0237 |

* cited by examiner

*Primary Examiner* — Manuel Mendez
(74) *Attorney, Agent, or Firm* — Laurence Weinberger

(57) ABSTRACT

A devise for retracting or opening a tissue wound employs two retractor arms that do not enter or penetrate into the wound. The retractor arms engage the tissue on either side of the wound and apply outward pressure on the tissue surface to open the wound.

20 Claims, 9 Drawing Sheets ved
TISSUE RETRACTOR

This application is a Continuation-in-Part application of U.S. patent application Ser. No. 14/298,334 filed on Jun. 6, 2014, the benefit of which is claimed. Additionally, the benefit of U.S. Provisional Application No. 61/832,531 filed Jun. 7, 2013, No. 61/857,234 filed Jul. 22, 2013, and No. 61/878,530 filed Sep. 16, 2013 are hereby claimed.

BACKGROUND OF THE INVENTION

Field of the Invention

Diseases resulting from tick bites are becoming epidemic. Deer tick bites, in particular, have been implicated in the spread of Lyme disease, and efficient methods of dealing with the bites are disclosed. Prompt removal of the tick and treatment with a bactericide may help prevent subsequent infections.

Description of Problem and Prior Art

Ticks are known to carry and transmit several diseases including Rocky Mountain spotted fever and Lyme disease. The prevalence of these tick borne diseases, particularly Lyme disease, has recently reached epidemic proportions in parts of the United States. It has been determined that it takes time after the initial tick bite for the pathogen to transfer from a tick into and through skin. Accordingly, prompt removal of a tick after it is noticed provides a first line of defense against infection.

Removal of a tick without causing it to inject the pathogen turns out to be very difficult. Recommendations of various sources regarding the necessity and removal of ticks are summarized in Appendix "A". The information emphasizes that during the difficult removal process, the individual should not damage, irritate, agitate, puncture, crush, squeeze or break the tick. If one or more of these unfortunate occurrences should happen, the pathogen in the saliva glands in the forward portion or further back in the body of the tick can be expelled deep into the wound. Doctors state that it is extremely difficult to remove an imbedded tick, particularly a very small deer tick, without causing one or more of the above listed items to occur. This is the case since ticks have a barbed hypostome that anchors the tick in the skin. With just a washing of the general area, it is clearly very difficult to kill the pathogen in the depth of a bite wound in which a tick has also deposited salivary cement on walls of the wound. The pathogen bonds to the tick's saliva protein (known as SALP 15 protein) as a cloaking device. As a result, a very large number of people may now have Lyme disease or other tick borne diseases because they only used soap and water or alcohol to wash off the general area of the bite.

An approach is needed that will kill the pathogen deep in the wound and quickly separate the SALP 15 protein and pathogen from the wound and immediate area. In the case of Lyme disease, for example, because the deer tick does not expel the pathogen for many hours after it has embedded and then many times expels on removal, such an approach provides the opportunity to kill pathogens at the wound site before they get into the blood circulatory system.

DETAILED DESCRIPTION OF THE INVENTION

Definitions

Figure 1:
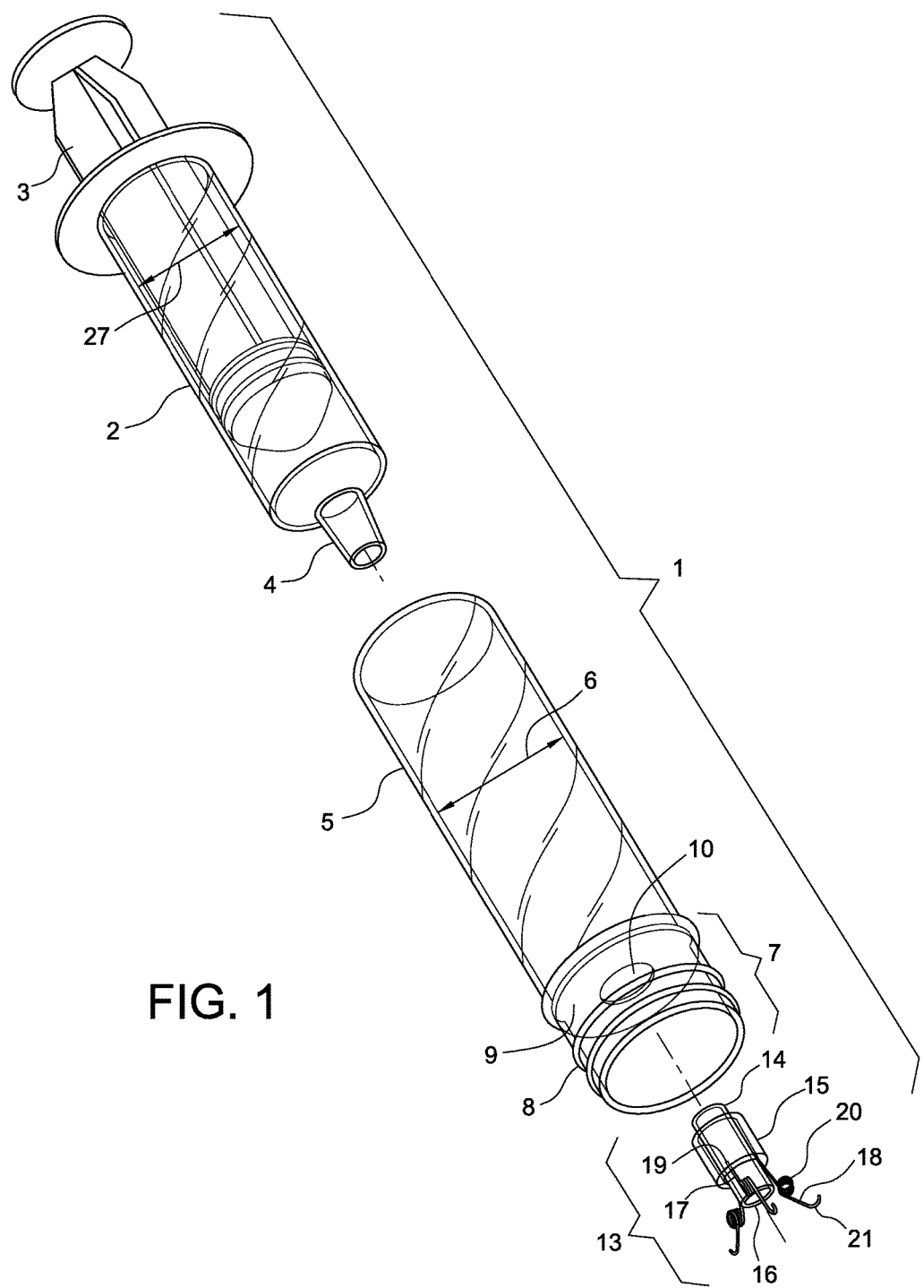
FIG. 1 shows a partially exploded view of the interceptor.

In the following description of the invention, DISTAL refers to the end of the device or its parts that will be closest to the site of application against skin during use.

In the following description of the invention, ANTERIOR refers to the end of the device or its parts that will be furthest from the site of application against skin during use.

DESCRIPTION

The present invention provides an interceptor device and method by which pathogens deposited by tick wound or other types of small wounds may be killed or significantly reduced in number before having an opportunity to enter the blood stream.

The present invention provides a tissue retractor that may be used to open and hold open small wounds.

In the figures like numbers denote the same part. However, as will be noted later in discussing an alternative embodiment, the assembly initially identified as 13 will be referenced as assembly 36 in order to distinguish the two arm retractor embodiment. With reference to the Figures, the interceptor device 1 of the invention comprises of a flushing needleless syringe 2 with plunger 3 which has an elongated dispensing conical tip 4. A splash shield 5 has an inner diameter 6 larger than the outer diameter 27 of syringe 2 so that syringe 2 may pass into splash shield 5. Once assembled, splash shield 5 surrounds the discharge conical tip 4 of syringe 2. The distal end 7 of shield 5 is transparent so that the areas of contact of the device with the skin can be observed. End 7 may have guide rings 8. Shield 5 has a retaining ring 9 located near its distal end 7. Retaining ring 9 has a centrally located circular opening 10.

A spreading and delivery assembly 13 attaches to conical tip 4. Spreading and delivery assembly 13 consists in part of two concentrically mounted tubes 14 and 15. The outside diameter of tube 14 approximates the interior diameter of tube 15. Tube 14 extends beyond the distal end of tube 15 and forms a discharge port or nozzle 16. The anterior end of tube 14 extends beyond the anterior end of tube 15 then through opening 10 of retaining ring 9 of shield 5 and couples the spreading and delivery assembly 13 by compressively mounting at 22 onto conical tip 4 of syringe 2. The exterior of tube 15 fixedly engages the opening 10 in retaining ring 9.

The anterior ends 17 of several stiff but flexible spreader arms 18 are captured and firmly held in place at 19 between the outer surface of tube 14 and the inner surface of tube 15 at the distal end of tube 15. Spreader arms 18 extend distally below the distal ends of tubes 14 and 15 and further consist of spring coils 20 located approximately about half the length of the spreader arms 18. The distal ends of spreader arms 18 are rounded to form contact surfaces 21. When mounted to conical tip 4, the spreader and delivery assembly 13 extends the distal end of tube 14 and spreader arms 18 below the distal end 7 of splash shield 5. A fill tube 28 having an interior diameter slightly greater that the exterior diameter of tube 14 may be temporarily placed onto nozzle 16. A wound or a tick bite is schematically shown at 23 on the skin surface 24.

The interceptor device of this invention is intended to be used with an appropriate antipathogen or antimicrobial. Exemplary antipathogens for use against tick borne pathogens include alcohol and possibly chlorhexidine.

Method of Use:

The following steps outline the general overall procedure for proper use of the interceptor device.

1) Before attempting to remove a tick, prepare the interceptor. The syringe 2 may be filled by placing the spreading and delivery assembly 13 sufficiently below the surface of an antipathogen solution so that withdrawal of the syringe plunger 3 draws antipathogen solution up into the syringe. Alternatively, a filling tube 28 may be placed onto nozzle 16 through which to draw antipathogen solution into the syringe. Set the interceptor aside.

2) After finding the tick which is embedded in the skin (or other applicable shallow insect bite wounds), using a pen or similar device mark the wound location with a small circle (about ¼" in diameter). This allows better visualization of the bite and more accurate centering. Since the tick can expel pathogen for the first time during removal, be careful to remove the tick as described at The Centers for Disease Control web site.

Figure 2:
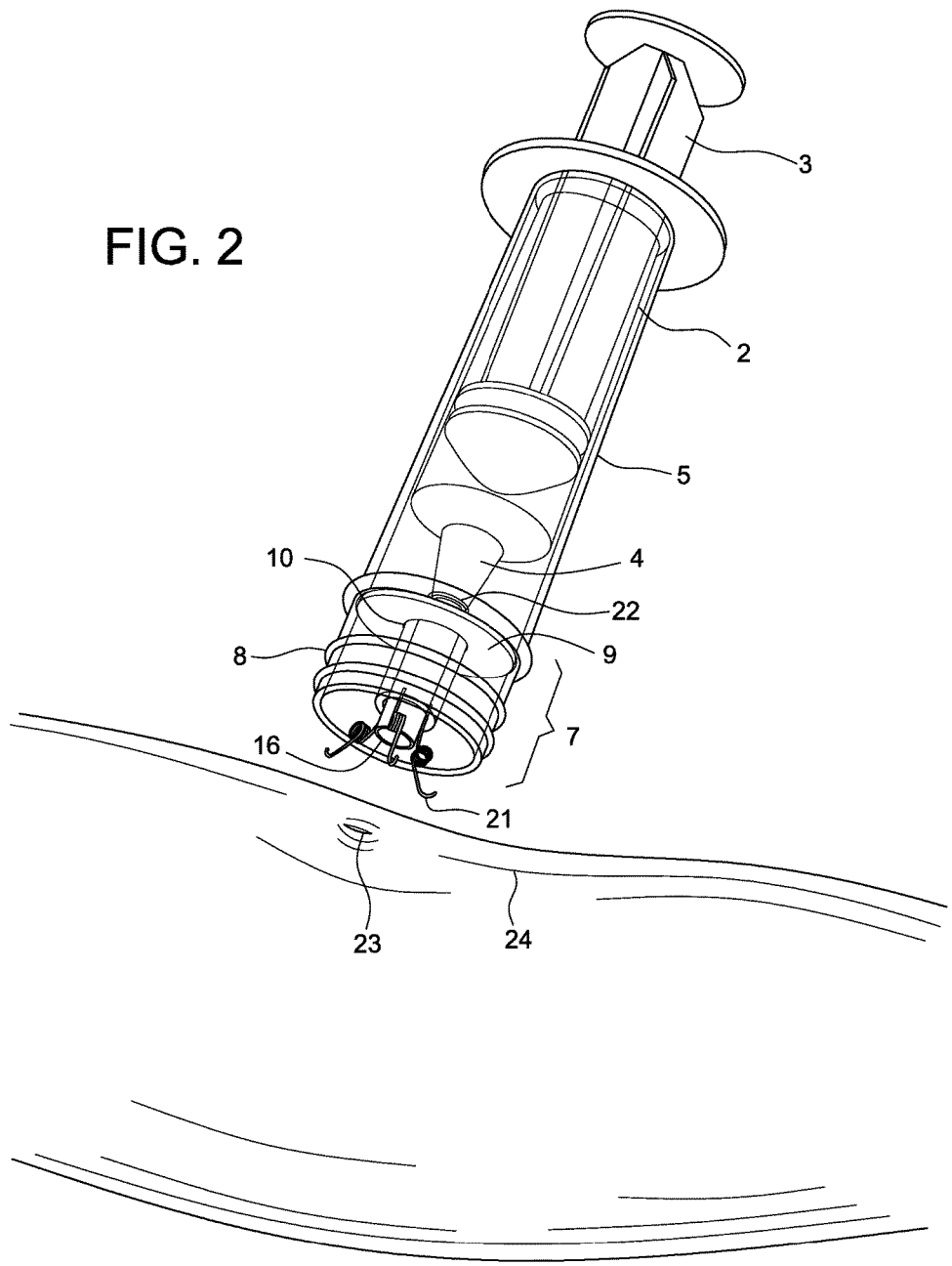
FIG. 2 shows the interceptor as it is moved towards the skin surface.
Figure 3:
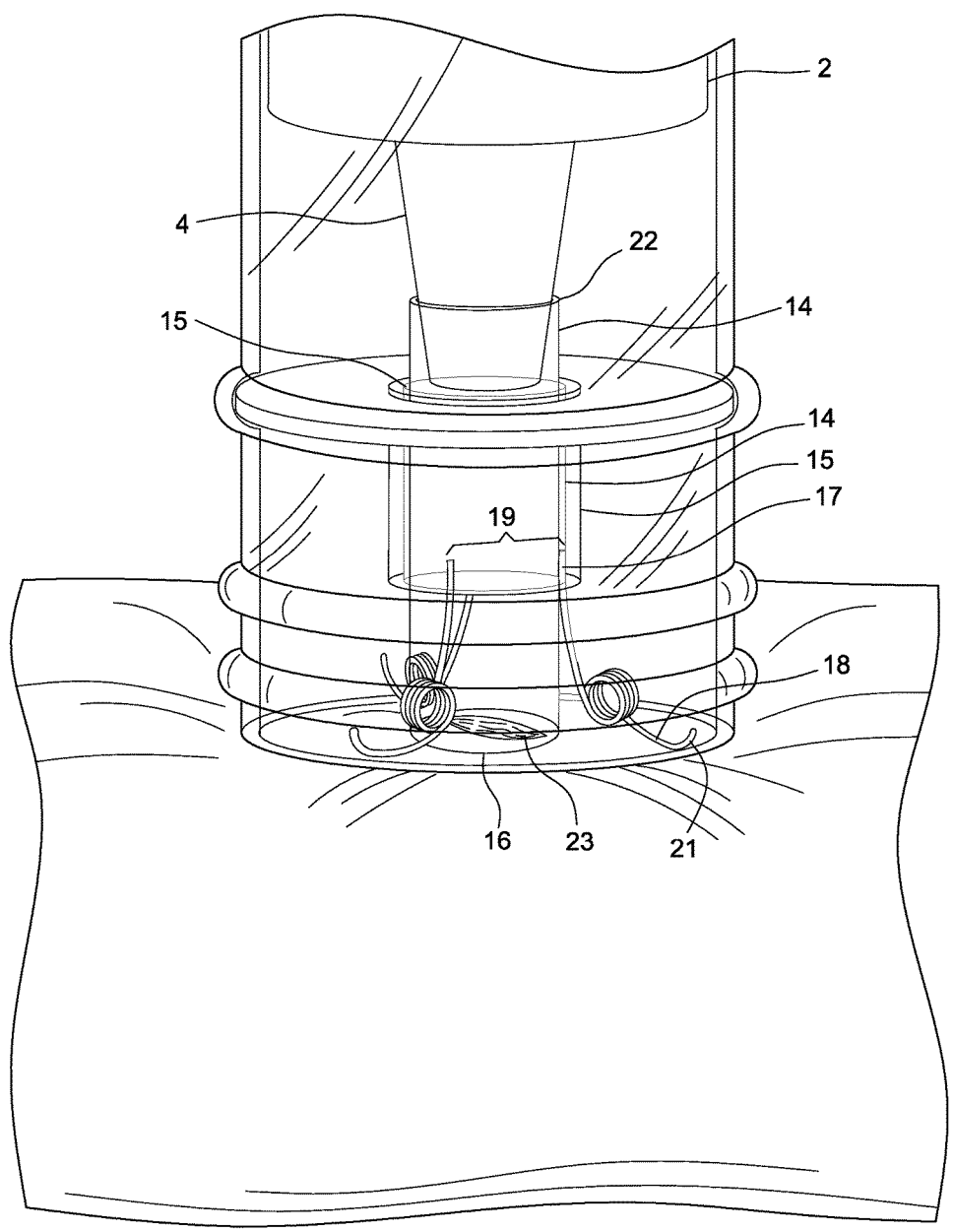
FIG. 3 shows the nozzle of the interceptor firmly pressed against the skin over a wound, the spreader arms engaging and tensioning the skin around the wound, and the splash shield engaging the surface of the skin.

3) Disinfect the wound area with rubbing alcohol or other antipathogen recommended for use on Lyme disease pathogens 4) Immediately move the interceptor 1 slowly towards the wound 23 in skin surface 24 as shown in FIG. 2 centering nozzle 16 as well as possible on wound 23. The interceptor should be applied substantially perpendicularly to skin surface 24 so that all the spreader arms 18 contact the skin at the same time. As the contact surfaces 21 of the spreader arms 18 engage the skin, they simultaneously apply pressure to tighten the skin in the immediate area of the wound in a direction outward from the wound center. The coils 20 in spreader arms 18 permit flexible movement of the spreader arms as contact with the skin is made. Continue moving the interceptor until nozzle 16 contacts and is pressed firmly against the skin around wound 23 and the splash shield 5 contacts the skin surface as shown in FIG. 3.

5) Thoroughly flush the wound multiple times by advancing the syringe piston 3 to force the alcohol or other antipathogen solution into and around the wound. Splash shield 5 protects the user from direct spray. For each flush, keep nozzle 16 pressed against the skin 24 and maintain the solution pressure generated by the syringe on the wound for several seconds in a constant manner. It is suggested that a minimum of three flushes be used with a duration of at least 5 seconds each.

6) After the last flush, leave nozzle 16 in contact with skin 24 and partially withdraw syringe piston 3 to apply suction to the wound to evacuate the contaminated fluids in the wound.

7) Empty the syringe by following standard household procedures for infectious liquids.

8) Attach the fill tube 28 to nozzle 16 and fill syringe 2 with clorhexidine or other different antipathogen by withdrawing the syringe plunger 3. Follow previous instructions for steps 4 through 6 above, but do not evacuate after the last flush.

9) Dispose of all leftover liquids, devices and materials in a safe manner for contaminated products. Disinfect your hands, gloves and equipment before and after the procedure.

Special Note: The treatment procedure outlined above should be done immediately (preferably 10 to 15 sec.) after the tick is removed. Every second counts to keep the pathogen out of the blood circulatory system and possibly prevent primary and secondary infections as well. A deer tick usually does not expel the pathogen (*Borrelia spirochete*) until after the tick has been embedded for several hours (refer to the CDC website); that is why it is critical to routinely examine the skin for tick attachments. Once the pathogen has entered the blood stream, the interceptor will no longer be useful to prevent or disinfect for tick borne disease. It is recommended that a doctor be seen immediately after use of the interceptor for follow up treatment.

As the interceptor is applied to the wound area, the ends 21 of spreader arms 18 contact the skin 24 first and then spread outwards from wound 23 pulling the skin around wound 23 slightly taut thereby tightening or retracting the skin away from the wound. In the FIGS. 1 through 4 of this patent document, three such spreader arms 18 are shown. However, in alternative embodiments a greater or lesser number of spreader arms 18 may be used. The important feature is that the spreader arms result in forming and positioning the wound opening to permit more efficient irrigation and better accessibility. At the same time, this tightening in a direction away from the center of the wound allows small cracks and crevices to open in the skin in the immediate area of the wound within the splash guard perimeter so that the antipathogen solution can enter. Using an antipathogen such as chlorhexidine in the last flush leaves some of the fluid in the wound and surrounding area to possibly continue killing any residual pathogens.

Using the interceptor as described not only treats just the wound opening but also the entire area within the splash guard area which experiences the highest count of pathogens. This specific process aids to continually, over a period of time, kill pathogens that can gradually escape from tubular mouthparts of the tick that often break off in the wound and are not immediately retrieved during the tick removal process. Sometimes these deeply imbedded mouthparts are never retrieved.

Preferably, the distal end 7 of the splash shield 5 is transparent so the user can see the wound and guide the interceptor to exactly center nozzle 16 on wound 23 in order to topically flush, irrigate and evacuate the wound. Guide rings 8 help the user to visualize the placement of the nozzle 16 onto wound 23. The splash guard 5 may be stored in a refrigerator to cool its distal end 7 that makes contact with the skin. Use of a cool splash guard may cool the skin in the immediate area of the wound to slow blood circulation in the immediate exposed capillaries to help contain the pathogen. This may contribute to a higher kill count of infection.

Figure 4:
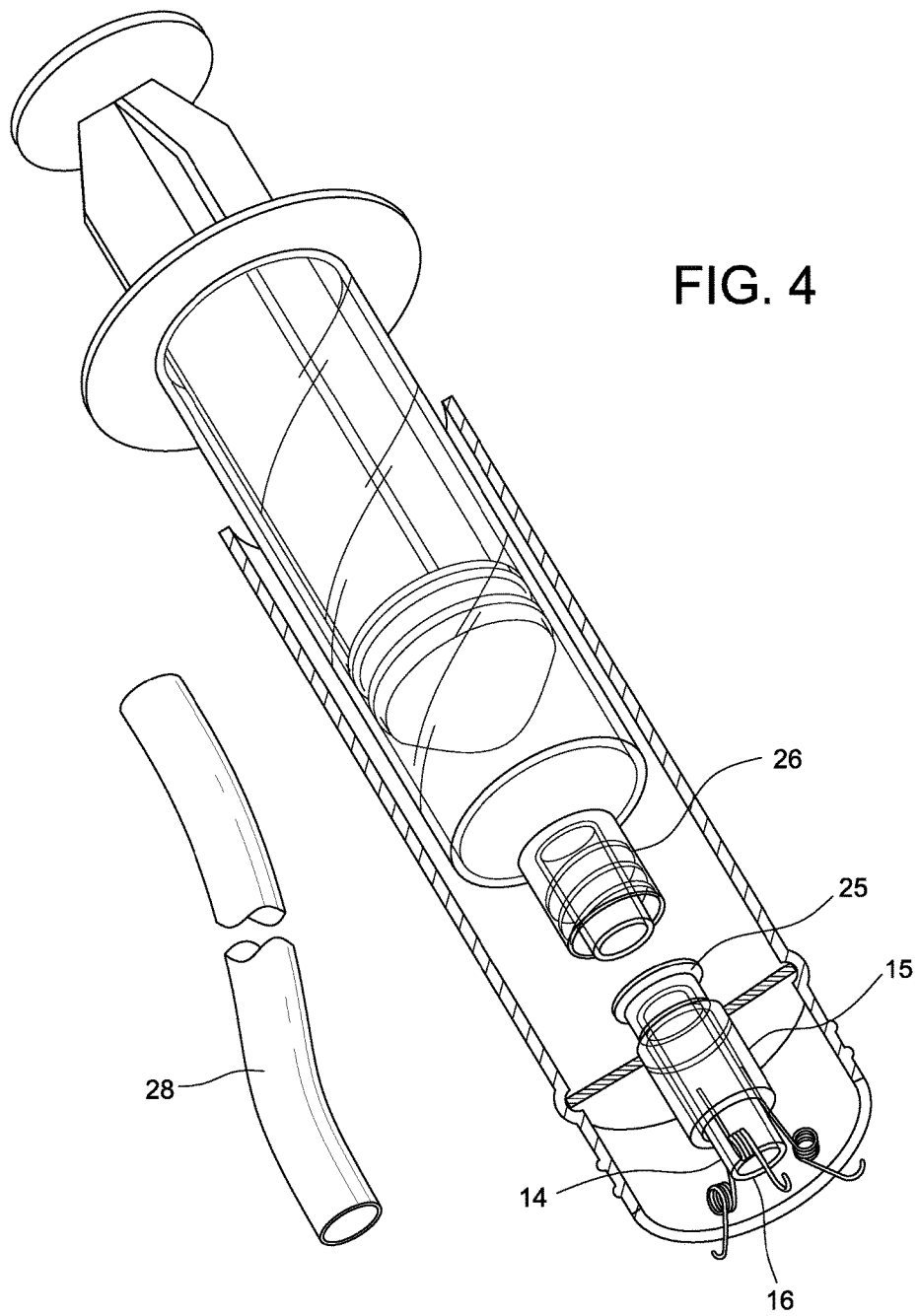
FIG. 4 shows an alternative embodiment in which the spreader and delivery assembly has a female luer lock 25 fastened at the anterior end of tube 14.
Figure 5:
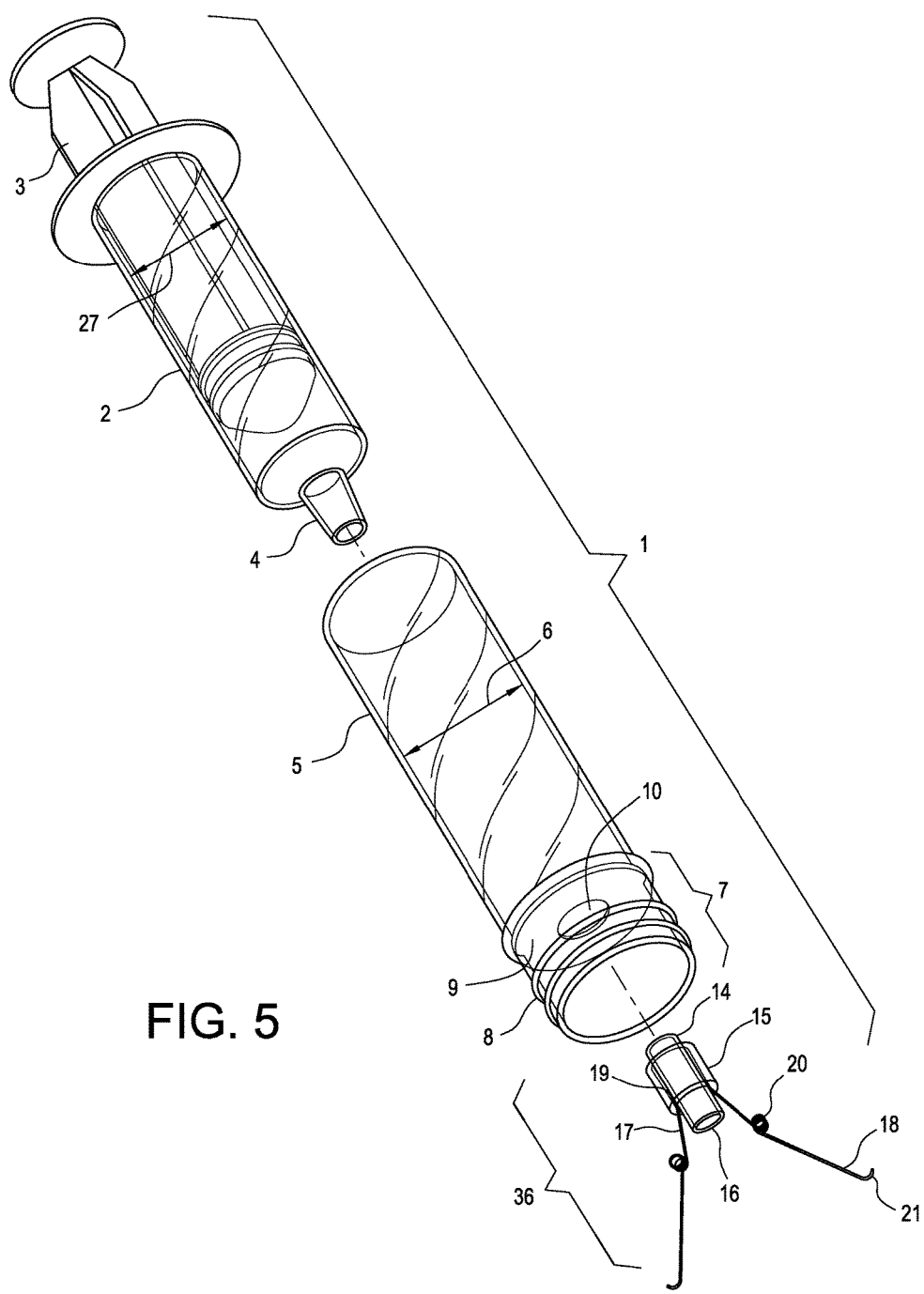
FIG. 5 shows the spreader and delivery assembly two arm retractor implementation with the arms on opposing sides of the assembly.
Figure 6:
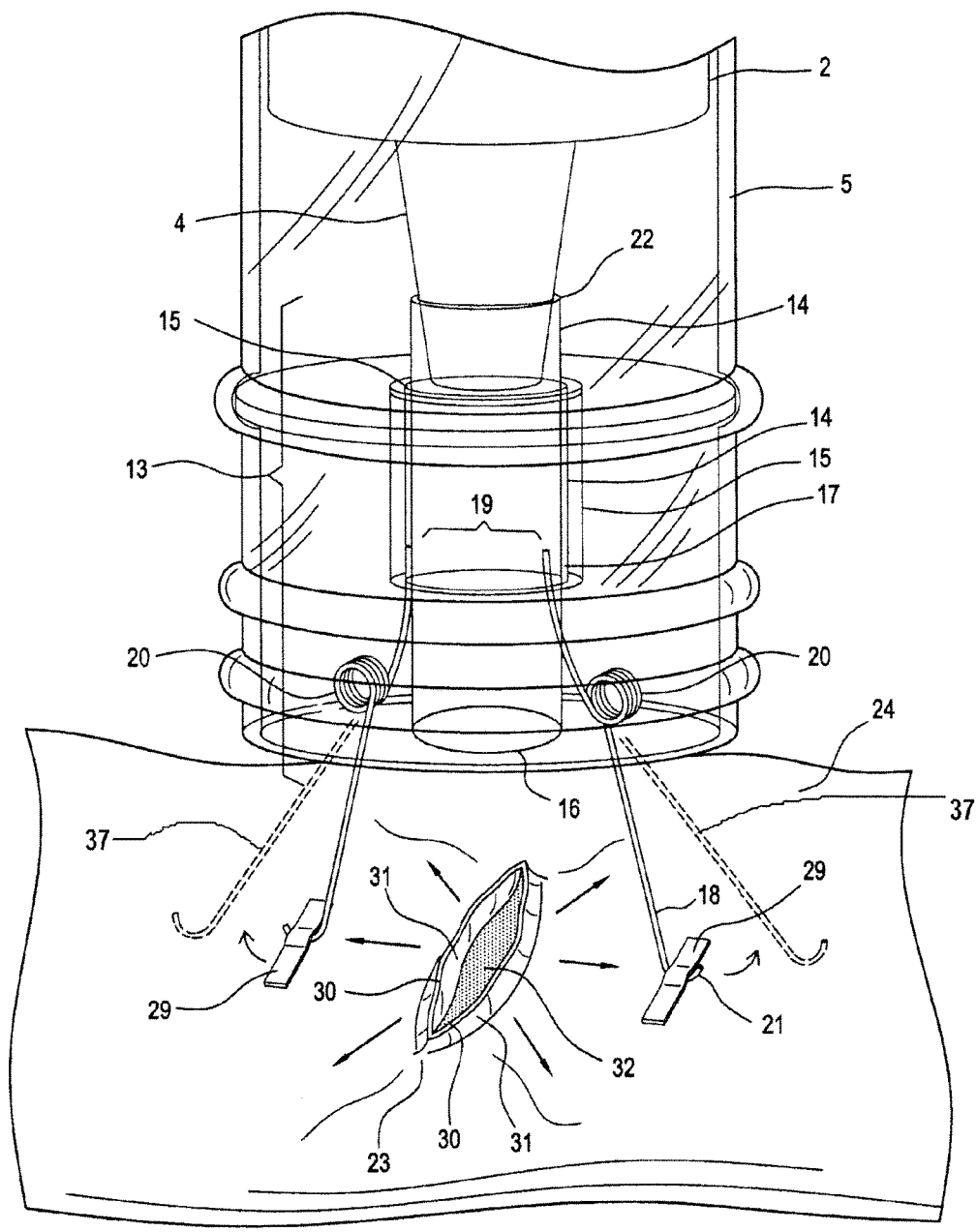
FIG. 6 depicts the two arm retractor spreader and delivery assembly with the retractor arms mounted on the syringe and anchored and engaged on the tissue surface.

In an alternative embodiment shown in FIG. 4, the spreader and delivery assembly 13 has a female luer lock 25 fastened at the anterior end of tube 14. The female luer lock 25 engages the male luer lock 26 of syringes that terminate with a male luer fitting thus permitting the spreader and delivery assembly 13 to be attached to and used with such syringes. Additionally, in yet another alternative embodiment, the nozzle 16 may be generally oval shaped in order to better approximate the shape of a wound.

The interceptor and method of the present invention provides a more thorough accessibility to the disease carrying organisms hidden in the hypostome salivary cement and the protein enhanced residuals that line the walls and the base of the wound. In the case of tick borne diseases like Lyme disease and Rocky Mountain spotted fever, these residuals add to the difficulty of making direct contact with the organisms. Use of the interceptor and the method may be applicable to other shallow insect wounds like spider bites as well as other small wounds not necessarily resulting from an insect bite. Alcohol in general has the capability to break down, denature and dilute proteins. In addition, the use of the interceptor and method of this invention could have a very significant impact on secondary infections.

Use of the interceptor is an alternative to traditional topical washing methods. The spreader arms and the nozzle of the interceptor are intended to overcome the natural inclination of the wound to close against the hypostome and protein salivary cement that impedes penetration of the antipathogen by increasing access of the antipathogen solution to the wound base and surrounding pores and crevices.

While the initial use of the invention has been described in conjunction with the treatment of a tick bite, in yet another embodiment, the apparatus of this invention may be employed, as noted above, as a tissue retractor to treat small tissue wounds or incisions. Typically, such wounds result not only from insect bites but also from small stones, debris, or glass that penetrate the surface of the skin. Alternatively, surgeries may involve small incisions in difficult to reach places where it is desired to open and hold open the incision without placing elements of a retractor within the incision.

For purposes of this disclosure of a retractor and its function, the spreader and delivery assembly, previous referenced and identified in the figures by numeral 13, will be, going forward and in FIGS. 5-9, referenced and identified by numeral 36 in order to clearly identify the two arm retractor version. In this embodiment, as seen in FIG. 5, the spreader and delivery assembly 36 utilizes only two spreader arms 18 substantially located 180 degrees apart on opposite sides of tube 14. It is important that arms 18 be located opposite each other to work against each other to retract a wound equally from both sides of wound 23.

In the present embodiment, spreader arms 18 are much longer than in the above described embodiments and extend well below the distal end of splash shield 5 so that, in their initial position before application to the tissue surface, arms 18 extend beyond the outside diameter of splash shield 5 as shown at position 37 in FIG. 6. It is a significant feature of this embodiment as a tissue retractor that the spreader arms extend beyond the outside diameter of splash shield 5. Clearly, in this present embodiment, splash shield 5 is not intended to and can never touch the tissue surface 24 without interfering with the action of spreader arms 18. However, splash shield 5 provides a suitable handle with which to grasp/manipulate the retractor. In addition to the restoring action of the coils 20, the material from which the longer spreader arms are made also provide additional resilience to displacement. Arms 18 made with material with greater resistance to displacement may be employed depending on the spreading force requirement for particular tissues. Typically, the arms are formed from stainless steel which may be disinfected so that the retractor may be used in medical settings.

The spreader arms 18 may be anchored to the tissue surface 24 by means of, but not limited to, adhesive strips, pins, and adhesives. The ends/contact surfaces 21 of arms 18 may be adapted to particular anchoring means as will be well understood by those skilled in the art. For example a longer end 21 may be provided for use with adhesive anchoring strips 29 as shown in FIG. 6. Alternatively, an end 39 with a slight hook may be provided to engage a pin 38 as shown in FIG. 7. Where appropriate, the anchoring means may be applied to the tissue surface 24 before the retractor arms 18 are engaged. As a further example, the ends/contact surfaces 21 of the spreader arms may be coated with a soft adhesive so that, as they engage the tissue surface 24, the ends/contact surfaces 21 are anchored to the tissue.

In order to use the wound retractor of this application, the longer arms 18 may be pinched together or inwardly by the user, and, after engaging one of the anchoring means, released. The combined resiliency of the material of which arms 18 are made in addition to the resiliency of the coils 20 provides an outward thrust thereby opening the wound or incision 23 to the appropriate shape for the intended procedure. Not only do coils 20 provide additional outward thrust to arms 18 but they also provide for a change of pitch of the spreader arms 18 providing an upward component (away from the plane of the tissue 24) to achieve the desired wound topography.

Anchored in this manner, the outward thrust of the spreader arms, indicated by the arrows on the tissue surface in FIG. 6 and FIG. 7, increases as spreader and delivery assembly 36 is moved towards the tissue surface 24 increasing the pressure applied by the spreader and delivery assembly 36. The coils 20 in spreader arms 18 are essential to enabling the spreader arm ends/contact surfaces 21 to move downward and outward in the desired manner by maintaining outward thrust even as more pressure is exerted by the decreasing distance of the spreader and delivery assembly 36 above tissue surface 24.

Utilized in this manner, the spreader arms 18 position the wound or incision 23 in a specific topography and shape. Unlike prior art retractors, which must be invasively inserted into a wound, the spreader arm retractors 18 of this embodiment do not intrude into the wound or incision 23. The spreader arm retractors 18 do not just tighten the skin/tissue on either side of the wound or incision 23 but, most importantly, also open the wound or incision 23 and pucker its shape. The outward thrust of spreader retractor arms 18 causes the wound to take on a specific puckered shape by rotating both tops 30 of the wound or incision walls 31 away from the center of the wound or incision 23 thereby exposing the base 32 of the wound and more surface area for thorough access. A topography is developed in which the tops of the wound or incision walls 30 rise above the surrounding tissue surface 24 thereby permitting debris, such as small shreds of glass or gravel, to flow away from the wound or incision 23 during irrigation. Puckering also raises the base 32 of the wound or incision 23, which is important for complete flushing, and removal of any contamination. The puckered wound or incision 23 forms a small reservoir or retention area for any liquid which may be administered through nozzle 16. In some cases, it may be advantageous for the liquid administered by the user to puddle up in the puckered wound or incision 23 for a given exposure interval. The result of the application of the spreader arms 18 of the present invention is a uniquely shaped incision or wound accomplished noninvasively. A singular and great advantage of the retractor system of the present invention is that the spreader arms are not engaged inside the wound as is the case with prior art retractors. Since the arms are not in the wound, greater access is permitted to the wound both for flushing and for retrieval of debris from the wound.

Figure 8:
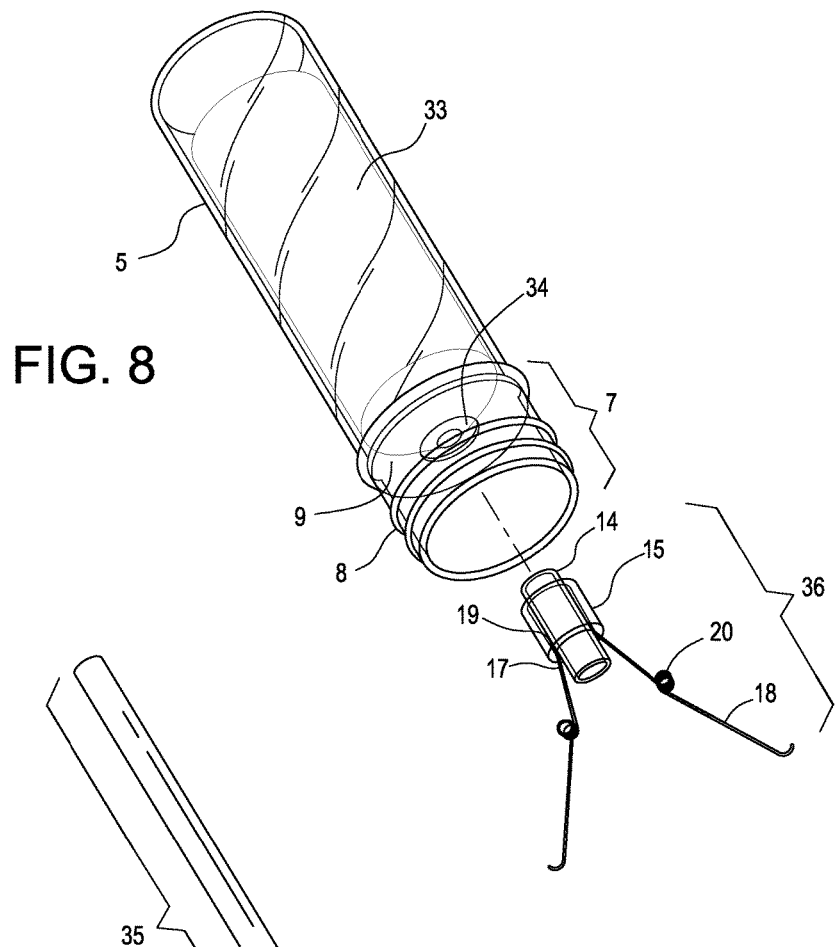
FIG. 8 shows a flashlight with illumination lamp inserted into the splash shield.

In a further embodiment, the splash guard shield 5 may be removed so that the user may access the wound with necessary implements such as tweezers for removal of debris. Without the splash guard, it is also possible to use a magnifier to better visualize the puckered wound during the desired process. To further aid in visualizing the wound, a light source directed into the wound may be attached to the side of syringe 2 (not shown). Alternatively, an illumination source such as a flashlight 33 having a light source 34 as shown in FIG. 8 may be placed within the splash shield 5 to illuminate the wound directly from above.

Figure 7:
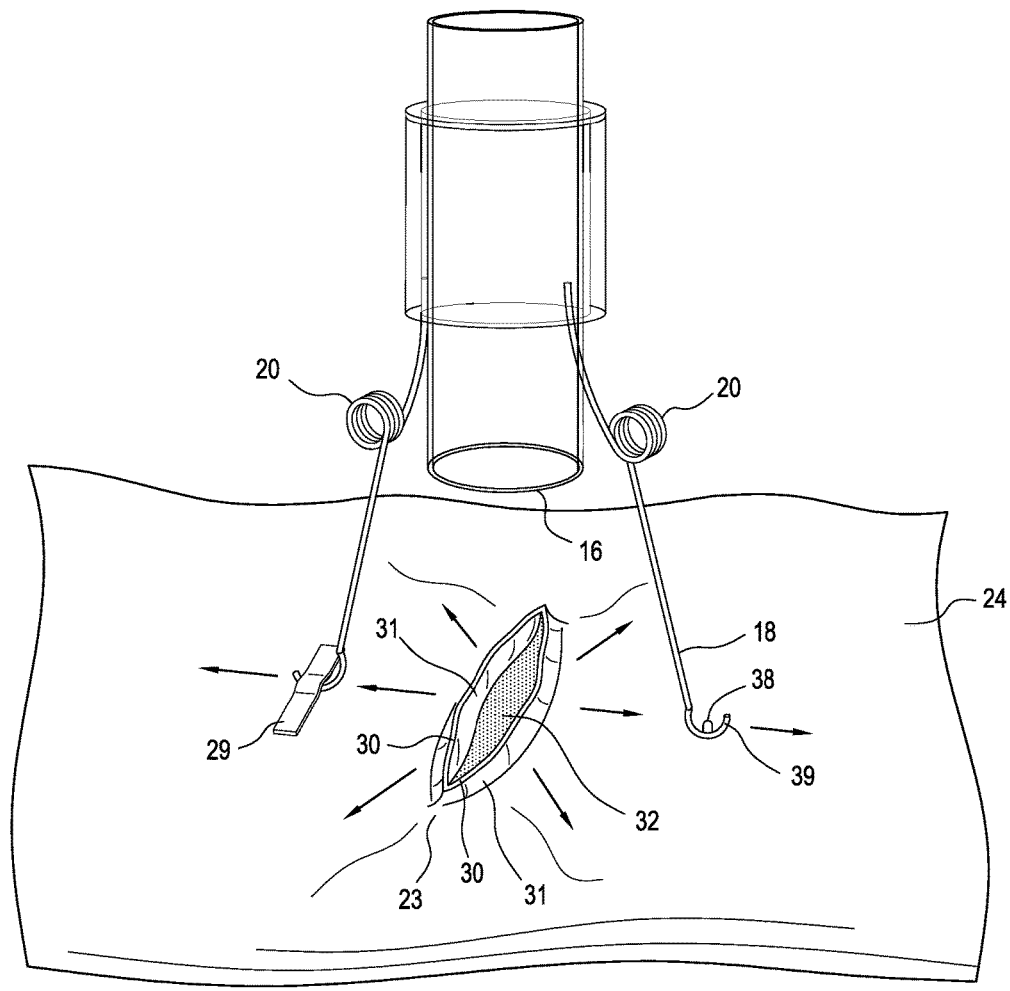
FIG. 7 depicts the two arm retractor spreader and delivery assembly separate from the syringe and anchored and engaged on the tissue surface.
Figure 9:
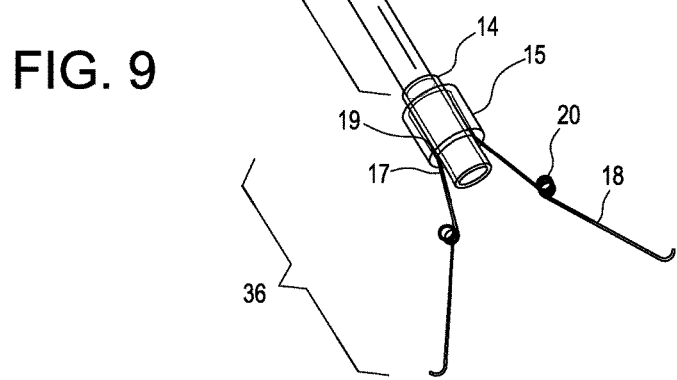
FIG. 9 shows a handle mounted into the two arm retractor spreader and delivery assembly.

In certain circumstances, it may be unnecessary or undesirable to utilize a syringe 2 to support the spreader and delivery assembly 36. For instance, when it is necessary to access an incision or wound in a limited area such as in one of the body openings, the larger body of the syringe would limit access. In this embodiment, the spreader and delivery assembly 36 may be dismounted from the syringe 2 and used as a stand alone spreader as shown in FIG. 7. In an alternative embodiment, the spreader and delivery assembly 36 may be mounted on the end of a long handle 35 shown in FIG. 9 which may either be inserted into tube 14 or have an appropriate luer lock 25 fastened to its end. The handle 35 may be hollow so that fluid may be passed through it for application to the wound. Again, to further aid in visualizing the wound, a light source (not shown) directed into the wound may be attached to the side of handle 35.

Figure 10:
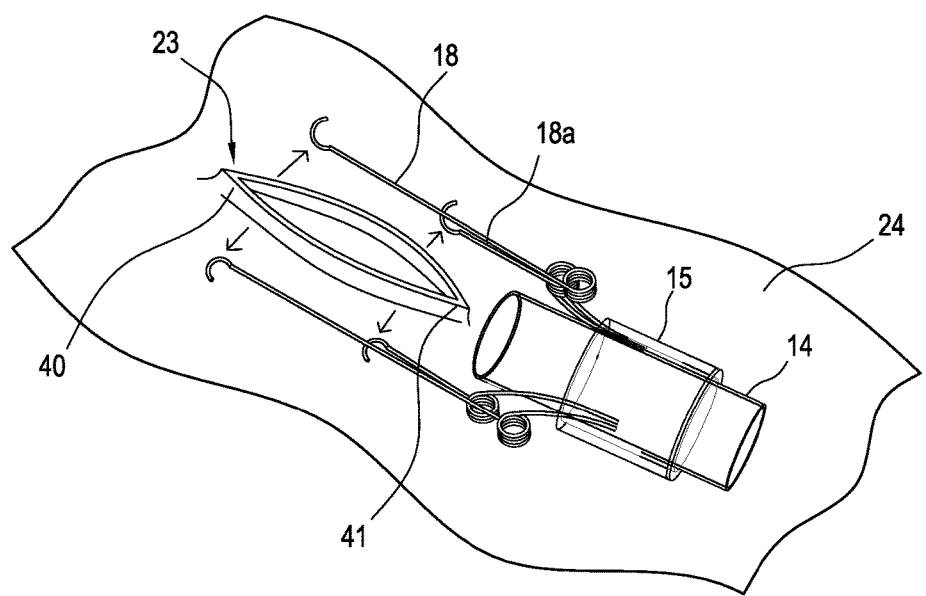
FIG. 10 depicts the spreader and retractor delivery assembly with two pairs of retractor arms with each member of the pair engaged on the tissue surface

In yet another embodiment shown in FIG. 10, the spreader arms of assembly 36 consist of two pairs of arms each pair opposed to the other pair on opposite sides of tube 14. The two arms making up each pair are mounted side by side between tubes 14 and 15. One member 18 of each pair is longer than the other member 18a. In this embodiment, assembly 36 is placed along the surface of tissue 24 (rather than perpendicular to it) adjacent to wound 23. The longer arms 18 act to retract one end of wound 23 while the shorter arms 18a act to retract the other end of wound 23. Each arm has a coil 20. The arms may be anchored in any of the previously described manners.

Those skilled in the art will appreciate that various modifications and alterations may be made to the device and method described in this patent document and such are considered to fall within the scope of this disclosure and appended claims.

The invention claimed is:

1. A non-invasive apparatus for retracting and flushing skin wounds comprising:
   a) a syringe having a projecting extension at its delivery end through which fluid may be drawn into and expelled from the syringe; and
   b) a retraction and fluid delivery assembly further comprising:
      i) a fluid delivery tube having at a first end a means for attaching the tube to the syringe projecting extension and having at a second end a nozzle; and
      ii) two stiff but flexible retractor spreader arms fixedly attached at the nozzle end of the delivery tube and disposed about the tube in positions substantially 180 degrees apart, the spreader arms extending beyond the nozzle end of the delivery tube;
      iii) spring coils located approximately about half the length of each spreader arm; and
      iv) means at the ends of each arm for engaging anchoring means at the skin surface
   wherein the spreader arms and coils flexibly apply pressure to the skin surface to tighten and retract the skin in the immediate area of the wound in a direction outward from the wound center.

2. The apparatus of claim 1 in which the means at the ends of each arm for engaging anchoring means are adapted to anchored in place by adhesive means.

3. The apparatus of claim 1 in which the means at the ends of each arm for engaging anchoring means are adapted to be anchored in place by non-slip material.

4. The apparatus of claim 1 in which the means at the ends of each arm for engaging anchoring means are adapted to be anchored by mechanical attachment.

5. A non-invasive apparatus for retracting skin wounds comprising:
   a) a central support;
   b) two stiff but flexible spreader arms fixedly attached at their first end to the central support and disposed about the support in positions substantially 180 degrees apart, the spreader arms extending beyond the end of the central support;
   c) means located at the second end of each arm for engaging anchoring means at the skin surface
   wherein the spreader arms flexibly apply pressure to the skin surface to tighten and retract the skin in the immediate area of the wound in a direction outward from the wound center.

6. The apparatus of claim 5 in which spring coils are located approximately about half the length of each spreader arm.

7. The apparatus of claim 5 in which the means at the ends of each arm for engaging anchoring means are adapted to anchored in place by adhesive means.

8. The apparatus of claim 5 in which the means at the ends of each arm for engaging anchoring means are adapted to be anchored in place by non-slip material.

9. The apparatus of claim 5 in which the means at the ends of each arm for engaging anchoring means are adapted to be anchored by mechanical attachment.

10. The apparatus of claim 5 in which the two spreader arms comprise two pairs of flexible spreader arms fixedly attached at their first end to the central support and each pair is disposed about the support in positions substantially 180 degrees apart.

11. The apparatus of claim 10 in which spring coils are located approximately about half the length of each spreader arm.

12. The apparatus of claim 10 in which the means at the ends of each arm for engaging anchoring means are adapted to anchored in place by adhesive means.

13. The apparatus of claim 10 in which the means at the ends of each arm for engaging anchoring means are adapted to be anchored in place by non-slip material.

14. The apparatus of claim 10 in which the means at the ends of each arm for engaging anchoring means are adapted to be anchored by mechanical attachment.

15. The apparatus of claim 10 in which one spreader arm of each pair is longer than the other spreader arm of the pair.

16. The apparatus of claim 15 in which spring coils are located approximately about half the length of each spreader arm.

17. The apparatus of claim 15 in which the means at the ends of each arm for engaging anchoring means are adapted to anchored in place by adhesive means.

18. The apparatus of claim 15 in which the means at the ends of each arm for engaging anchoring means are adapted to be anchored in place by non-slip material.

19. The apparatus of claim 15 in which the means at the ends of each arm for engaging anchoring means are adapted to be anchored by mechanical attachment.

20. A method of non-invasively spreading a skin wound using the retractor of claim 15 in which the retractor is placed substantially parallel to the skin surface with the shorter spreader arms of each pair placed near the end of the wound closest to the central support and the longer spreader arms placed further away.

* * * * *